(12) United States Patent
Brazdil et al.

(10) Patent No.: US 8,455,388 B2
(45) Date of Patent: *Jun. 4, 2013

(54) ATTRITION RESISTANT MIXED METAL OXIDE AMMOXIDATION CATALYSTS

(75) Inventors: James F. Brazdil, Glen Ellyn, IL (US); Mark A. Toft, Somonauk, IL (US); Michael J. Seely, Plainfield, IL (US); Charles J. Besecker, Batavia, IL (US); Robert A. Gustaferro, Naperville, IL (US)

(73) Assignee: INEOS USA LLC, Lisle, IL (US)

( * ) Notice: Subject to any disclaimer, the term of this patent is extended or adjusted under 35 U.S.C. 154(b) by 284 days.

This patent is subject to a terminal disclaimer.

(21) Appl. No.: 12/661,720

(22) Filed: Mar. 23, 2010

(65) Prior Publication Data
US 2011/0237821 A1 Sep. 29, 2011

(51) Int. Cl.
*C07C 51/16* (2006.01)
*C07C 51/215* (2006.01)
*B01J 27/128* (2006.01)
*B01J 27/132* (2006.01)
*B01J 27/06* (2006.01)
*B01J 23/28* (2006.01)
*B01J 23/76* (2006.01)
*B01J 23/887* (2006.01)

(52) U.S. Cl.
USPC ........... 502/205; 502/214; 502/304; 558/321; 558/322; 558/324

(58) Field of Classification Search
USPC .................. 502/205, 212, 304; 558/312, 322, 558/324
IPC .......... B01J 23/28,23/76, 23/887, 23/16, 23/20, B01J 23/34, 23/54, 23/00, 27/06, 27/128, B01J 27/132; C07C 51/16, 51/215
See application file for complete search history.

(56) References Cited

U.S. PATENT DOCUMENTS

| | | |
|---|---|---|
| 4,040,978 A | 8/1977 | Li |
| 4,139,552 A | 2/1979 | Grasselli et al. |
| 4,148,757 A | 4/1979 | Brazdil et al. |
| 4,168,246 A | 9/1979 | Li |
| 4,212,766 A | 7/1980 | Brazdil |
| 4,377,534 A | 3/1983 | Grasselli |
| 4,414,133 A | 11/1983 | Otake et al. |
| 4,746,753 A | 5/1988 | Brazdil et al. |
| 4,766,232 A | 8/1988 | Grasselli et al. |
| 4,863,891 A | 9/1989 | Grasselli et al. |
| 4,939,286 A | 7/1990 | Brazdil et al. |
| 5,093,299 A | 3/1992 | Suresh et al. |
| 5,134,105 A | 7/1992 | Paparizos et al. |
| 5,175,334 A | 12/1992 | Suresh et al. |
| 5,212,137 A | 5/1993 | Suresh et al. |
| 5,223,469 A | 6/1993 | Chen et al. |
| 5,235,088 A | 8/1993 | Paparizos et al. |
| 5,364,825 A | 11/1994 | Neumann et al. |
| 5,583,084 A | 12/1996 | Martin et al. |
| 5,583,086 A | 12/1996 | Tenten et al. |
| 5,658,842 A | 8/1997 | Midorikawa et al. |
| 5,663,113 A | 9/1997 | Midorikawa et al. |
| 5,780,664 A | 7/1998 | Aoki |
| 5,808,143 A | 9/1998 | Karrer et al. |
| 5,834,394 A | 11/1998 | Chen et al. |
| 5,840,648 A | 11/1998 | Suresh et al. |
| 5,877,381 A | 3/1999 | Sasaki et al. |
| 6,136,998 A * | 10/2000 | Sasaki et al. ................... 558/322 |
| 6,143,690 A | 11/2000 | Komada et al. |
| 6,420,307 B1 | 7/2002 | Wu et al. |
| 6,458,742 B1 | 10/2002 | Paparizos et al. |
| 6,479,691 B1 * | 11/2002 | Sasaki et al. ................... 558/321 |
| 6,723,869 B1 * | 4/2004 | Mori et al. ...................... 558/324 |
| 7,071,140 B2 * | 7/2006 | Paparizos et al. ............. 502/215 |
| 7,348,291 B2 * | 3/2008 | Paparizos et al. ............. 502/304 |
| 7,473,666 B2 * | 1/2009 | Yanagi et al. ................... 502/243 |
| 7,807,600 B2 | 10/2010 | Watanabe et al. |
| 2004/0030172 A1* | 2/2004 | Bogan, Jr. ....................... 558/322 |
| 2004/0063990 A1* | 4/2004 | Gaffney et al. ................. 558/322 |
| 2007/0160517 A1* | 7/2007 | Fan et al. ........................ 423/210 |
| 2009/0221843 A1* | 9/2009 | Watanabe et al. .............. 558/321 |
| 2009/0234149 A1* | 9/2009 | Miyaki et al. ................... 558/322 |
| 2009/0298673 A1* | 12/2009 | Akamine et al. ................ 502/65 |

FOREIGN PATENT DOCUMENTS

| | | |
|---|---|---|
| CN | 1114915 | 1/1996 |
| CN | 1230459 | 10/1999 |
| CN | 1310046 | 2/2000 |
| CN | 1287882 | 3/2001 |
| CN | 1302690 | 7/2001 |
| CN | 1310172 | 8/2001 |
| EP | 1223162 | 7/2002 |
| GB | 1436475 | 5/1976 |
| JP | 07047272 | 2/1995 |
| JP | 020045696 | 2/2002 |
| WO | WO0114057 | 3/2001 |
| WO | WO03033139 | 4/2003 |
| WO | WO2004050238 | * 6/2004 |

* cited by examiner

Primary Examiner — Jun Li
(74) Attorney, Agent, or Firm — David P. Yusko

(57) ABSTRACT

A catalytic composition useful for the conversion of an olefin selected from the group consisting of propylene, isobutylene or mixtures thereof, to acrylonitrile, methacrylonitrile, and mixtures thereof. The catalytic composition comprising a complex of metal oxides comprising bismuth, molybdenum, iron, cerium and other promoters, wherein the ratio of cerium to iron in the composition is greater than or equal to 0.8 and less than or equal to 5.

6 Claims, 3 Drawing Sheets

ATTRITION RESISTANT MIXED METAL OXIDE AMMOXIDATION CATALYSTS

REFERENCE TO RELATED APPLICATIONS

This application is related to (i) U.S. patent application. Ser. No. 12/661,716, entitled "Process for Preparing Improved Mixed Metal Oxide Ammoxidation Catalysts", filed Mar. 23, 2010 by Brazdil et al. now U.S. Pat. No. 8,258,073, and ii) U.S. patent application Ser. No. 12/661,705, entitled "Mixed Metal Oxide Ammoxidation Catalysts", filed Mar. 23, 2010 by Brazdil et al., now U.S. Pat. No. 8,153,546, both filed on the date even herewith, which are hereby incorporated by reference for all purposes.

BACKGROUND OF THE INVENTION

1. Field of the Invention

The present invention relates to an attrition resistant catalyst for use in the ammoxidation of an unsaturated hydrocarbon to the corresponding unsaturated nitrile. In particular, the present invention is directed to an improved catalytic composition for the ammoxidation of propylene and/or isobutylene to acrylonitrile and/or methacrylonitrile, respectively.

2. Description of the Prior Art

Catalysts containing oxides of iron, bismuth and molybdenum, promoted with suitable elements, have long been used for the conversion of propylene and/or isobutylene at elevated temperatures in the presence of ammonia and oxygen (usually in the form of air) to manufacture acrylonitrile and/or methacrylonitrile. In particular, Great Britain Patent 1436475; U.S. Pat. Nos. 4,766,232; 4,377,534; 4,040,978; 4,168,246; 5,223,469 and 4,863,891 are each directed to bismuth-molybdenum-iron catalysts which may be promoted with the Group II elements to produce acrylonitrile. In addition, U.S. Pat. Nos. 5,093,299, 5212,137, 5,658,842 and 5,834,394 are directed to bismuth-molybdenum promoted catalysts exhibiting high yields to acrylonitrile.

In part, the instant invention relates to an attrition resistant supported bismuth-molybdenum-iron catalysts promoted with cerium. It has been discovered that by controlling the relative amounts of these iron and cerium impacts the hardness of the catalyst. Prior art catalysts were often characterized by low ratios of Ce to Fe (e.g. less than about 0.7) which tended to produce softer less attrition resistant catalysts even when combined with a support material.

SUMMARY OF THE INVENTION

The present invention is directed to an attrition resistant mixed metal oxide catalyst for the ammoxidation of propylene and/or isobutylene.

In one embodiment, the invention is directed to a catalytic composition comprising a complex of metal oxides wherein the relative ratios of the elements in said catalyst are represented by the following formula:

$$Mo_{12}Bi_aFe_bA_cD_dE_eF_fG_gCe_hO_x$$

wherein A is at least one element selected from the group consisting of sodium, potassium, rubidium and cesium; and D is at least one element selected from the group consisting of nickel, cobalt, manganese, zinc, magnesium, calcium, strontium, cadmium and barium;

E is at least one element selected from the group consisting of chromium, tungsten, boron, aluminum, gallium, indium, phosphorus, arsenic, antimony, vanadium and tellurium;

F is at least one element selected from the group consisting of a rare earth element, titanium, zirconium, hafnium, niobium, tantalum, aluminum, gallium, indium, thallium, silicon, germanium, and lead;

G is at least one element selected from the group consisting of silver, gold, ruthenium, rhodium, palladium, osmium, iridium, platinum and mercury; and a, b, c, d, e, f, g, h and n are, respectively, the atomic ratios of bismuth (Bi), iron (Fe), A, D, E, F, cerium (Ce) and oxygen (O), relative to 12 atoms of molybdenum (Mo), wherein a is from 0.05 to 7,
b is from 0.1 to 7,
c is from 0.01 to 5,
d is from 0.1 to 12,
e is from 0 to 5,
f is from 0 to 5,
g is from 0 to 0.2,
h is from 0.01 to 5, and
x is the number of oxygen atoms required to satisfy the valence requirements of the other component elements present.

wherein $0.8 \leq h/b \leq 5$, and wherein the catalyst composition comprises a support selected from the group consisting of silica, alumina, zirconium, titania, or mixtures thereof, and wherein the support comprises between 30 and 70 weight percent of the catalyst composition.

The present invention is also directed to processes for the conversion of an olefin selected from the group consisting of propylene and isobutylene or mixtures thereof, to acrylonitrile, and/or methacrylonitrile, and other by-product nitriles (i.e. compounds having the function group "—CN", such acetonitrile and hydrogen cyanide) and mixtures thereof, by reacting in the vapor phase at an elevated temperature and pressure said olefin with a molecular oxygen containing gas and ammonia in the presence of an mixed metal oxide catalyst as described in the previous paragraph.

DETAILED DESCRIPTION OF THE INVENTION

Figure 1:
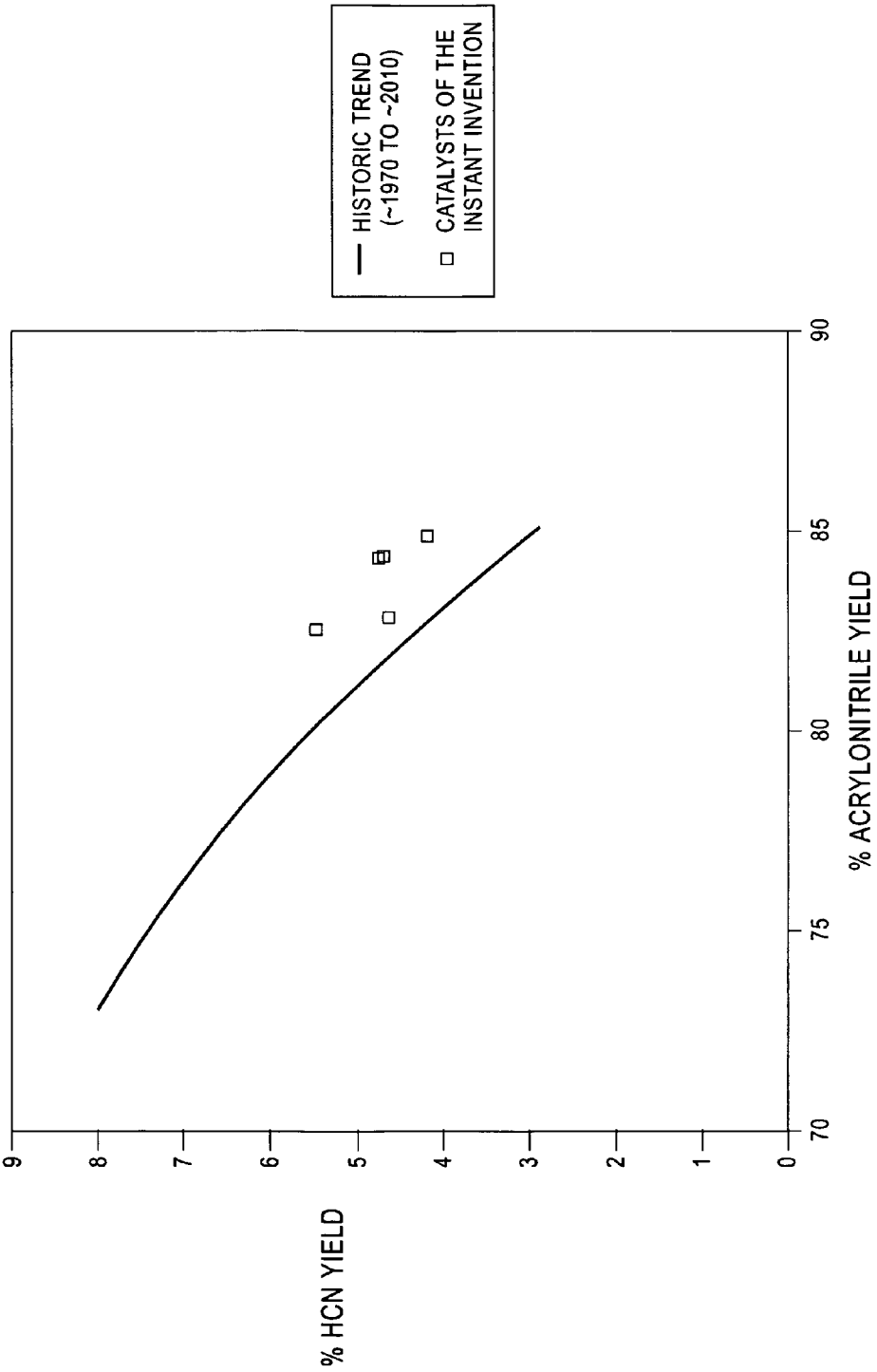
FIG. 1 is a plot of the historical trend with respect to acrylonitrile catalyst development showing Acrylonitrile Yield on the x-axis and Hydrogen Cyanide Yield on the y-axis. This plot illustrates that over time as Acrylonitrile Yield has been improved, the corresponding Hydrogen Cyanide Yield has decreased. The catalysts of the instant invention do not conform to this historical trend. The catalysts of the instant invention provide an increase in Acrylonitrile Yield without a significant decrease in Hydrogen Cyanide Yield as found in the historical trend.
Figure 2:
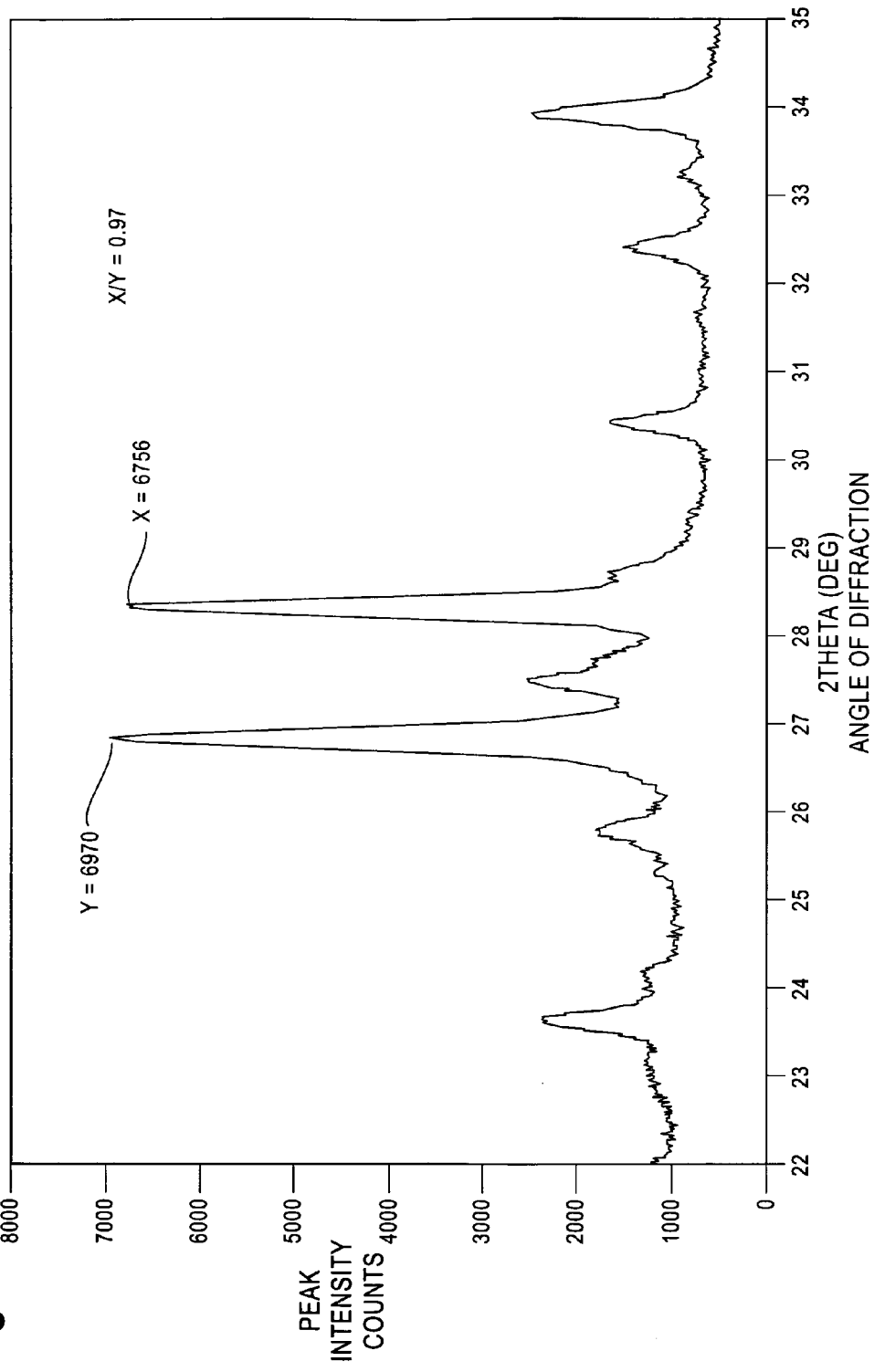
FIG. 2 is an XRD diffraction pattern or XRD diffractogram of a catalyst within the scope of the instant invention. This diffractogram illustrates an intense x-ray diffraction peak within 2θ angle 28±0.3 degrees (with the intensity defined as "X") and an intense x-ray diffraction peak within 2θ angle 26.5±0.3 degrees (with the intensity defined as "Y"). The ratio of X/Y is 0.97.
Figure 3:
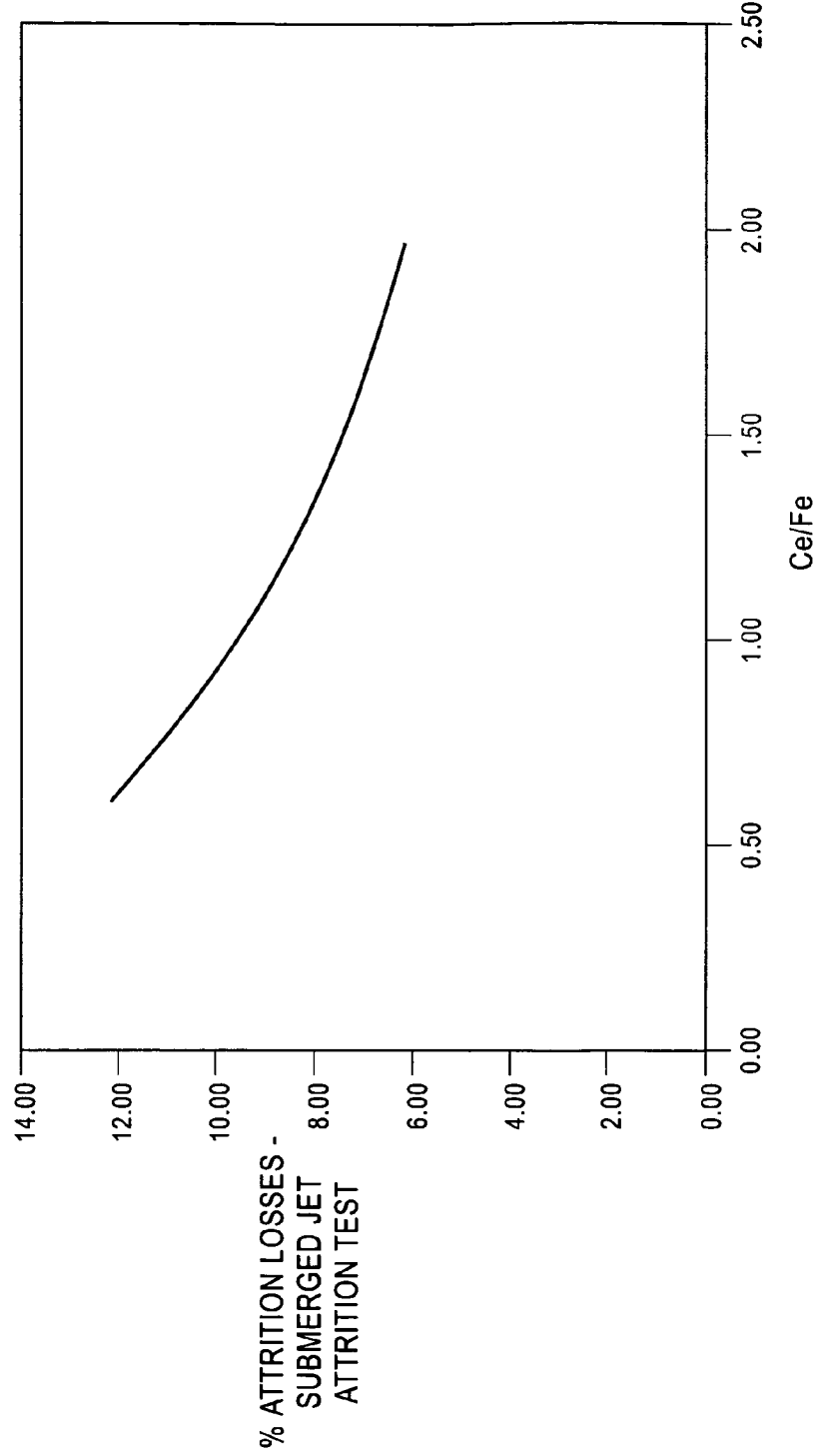
FIG. 3 is a plot of attrition resistance versus the Ce/Fe ratio in the catalyst. It has been discovered that catalysts having the compositions described herein and having a Ce/Fe ratio greater than or equal to 0.8 and less than or equal to 5 tend to be stronger in that they have a lower attrition loss as determined by a submerged jet attrition test.

The instant invention is a novel catalyst comprising a unique combination and ratio of promoters offering better performance in the catalytic ammoxidation of propylene, isobutylene or mixtures thereof, to acrylonitrile, methacrylonitrile and mixtures thereof, respectively The Catalyst:

The present invention is directed to a multi-component mixed metal oxide ammoxidation catalytic composition comprising a complex of catalytic oxides wherein the elements and the to relative ratios of the elements in said catalytic composition are represented by the following formula:

$$Mo_{12}Bi_aFe_bA_cD_dE_eF_fG_gCe_hO_x$$

wherein A is at least one element selected from the group consisting of sodium, potassium, rubidium and cesium; and D is at least one element selected from the group consisting of nickel, cobalt, manganese, zinc, magnesium, calcium, strontium, cadmium and barium;

E is at least one element selected from the group consisting of chromium, tungsten, boron, aluminum, gallium, indium, phosphorus, arsenic, antimony, vanadium and tellurium;

F is at least one element selected from the group consisting of a rare earth element, titanium, zirconium, hafnium, niobium, tantalum, thallium, silicon, germanium, and lead;

G is at least one element selected from the group consisting of silver, gold, ruthenium, rhodium, palladium, osmium, iridium, platinum and mercury; and a, b, c, d, e, f, g, h and n are, respectively, the atomic ratios of bismuth (Bi), iron (Fe), A, D, E, F, cerium (Ce) and oxygen (O), relative to 12 atoms of molybdenum (Mo), wherein a is from 0.05 to 7,
b is from 0.1 to 7,
c is from 0.01 to 5,
d is from 0.1 to 12,
e is from 0 to 5,
f is from 0 to 5,
g is from 0 to 0.2,
h is from 0.01 to 5, and
x is the number of oxygen atoms required to satisfy the valence requirements of the other component elements present.

In one embodiment of the above described catalytic composition, $0.15 \leq (a+h)/d \leq 1$. In another embodiment of the above described catalytic composition, $0.8 \leq h/b \leq 5$. In yet another embodiment, the X-ray diffraction pattern of the above identified catalytic composition has X-ray diffraction peaks at 2θ angle 28±0.3 degrees and 2θ angle 26.5±0.3 degrees and if the ratio of the intensity of the most intense x-ray diffraction peak within 2θ angle 28±0.3 degrees to the intensity of most intense x-ray diffraction peak within 2θ angle 26.5±0.3 degrees is defined as X/Y, then X/Y is greater than or equal to 0.7. In other independent embodiments of the above to identified catalytic composition: $0.2 \leq (a+h)/d \leq 0.6$; $0.3 \leq (a+h)/d \leq 0.5$; $1 \leq h/b \leq 3$; $1.5 \leq h/b \leq 2$; X/Y is greater than or equal to 0.8.; and/or X/Y is greater than or equal to 0.90.

In the embodiment, (where $0.8 \leq h/b \leq 5$), "h/b" represents the ratio of cerium to iron in the catalyst and for any catalyst formulation this ratio is simply the moles of cerium (as represented by the subscript for cerium in the formula) divided by the moles of iron (as represented by the subscript for iron in the formula). It has been discovered that catalysts described by the above formula wherein $0.8 \leq h/b \leq 5$ tend to be stronger in that they have a lower attrition loss as determined by a submerged jet attrition test.

In the embodiment, characterized by the X-ray diffraction pattern of the above identified catalytic composition having X-ray diffraction peaks at 2θ angle 28±0.3 degrees and 2θ angle 26.5±0.3 degrees and if the ratio of the intensity of the most intense x-ray diffraction peak within 2θ angle 28±0.3 degrees to the intensity of most intense x-ray diffraction peak within 2θ angle 26.5±0.3 degrees is defined as X/Y, then X/Y is greater than or equal to 0.7, it has been discovered that such catalysts provide greater overall conversion for the ammoxidation of propylene and/or isobutylene to nitriles (i.e. compounds having the function group "—CN", such as acrylonitrile, methacrylonitrile, acetonitrile and hydrogen cyanide As used herein, "catalytic composition" and "catalyst" are synonymous and used interchangeably. As used herein, a "rare earth element" means at least one of lanthanum, cerium, praseodymium, neodymium, promethium, samarium, europium, gadolinium, terbium, dysprosium, holmium, erbium, thulium, ytterbium, scandium and yttrium. As used herein, "2θ" is synonymous with "2 theta".

The catalyst of the present invention may be used either supported or unsupported (i.e. the catalyst may comprise a support). Suitable supports are silica, alumina, zirconium, titania, or mixtures thereof. A support typically serves as a binder for the catalyst and results in a stronger (i.e. more attrition resistant) catalyst. However, for commercial applications, an appropriate blend of both the active phase (i.e. the complex of catalytic oxides described above) and the support is crucial to obtain an acceptable activity and hardness (attrition resistance) for the catalyst. Typically, the support comprises between 40 and 60 weight percent of the supported catalyst. In one embodiment of this invention, the support may comprise as little as about 30 weight percent of the supported catalyst. In another embodiment of this invention, the support may comprise as much as about 70 weight percent of the supported catalyst.

In one embodiment the catalyst is supported using a silica sol. Typically, silica sols contain some sodium. In one embodiment, the silica sol contains less than 600 ppm sodium. In another embodiment, the silica sol contains less than 200 ppm sodium. Typically, the average colloidal particle diameter of the silica sol is between about 15 nm and about 50 nm. In one embodiment of this invention, the average colloidal particle diameter of the silica sol is about 10 nm and can be as low as about 4 nm. In another embodiment of this invention, the average colloidal particle diameter of the silica sol is about 100 nm. In another embodiment of this invention, the average colloidal particle diameter of the silica sol is about 20 nm.

Catalyst Preparation:

In one embodiment, the elements in the above identified catalyst composition are combined together in an aqueous catalyst precursor slurry, the aqueous precursor slurry so obtained is dried to form a catalyst precursor, and the catalyst precursor is calcined to form the catalyst. However, unique to the process of the instant invention is the following:

(i) combining, in an aqueous solution, source compounds of Bi and Ce, and optionally one or more of Na, K, Rb, Cs, Ca, a rare earth element, Pb, W and Y, to form a mixture (i.e. a first mixture), (ii) adding a source compound of molybdenum to the mixture (i.e. the first mixture) to react with the mixture and form a precipitate slurry, and (iii) combining the precipitate slurry with source compounds of the remaining elements and of the remaining molybdenum in the catalyst to form the aqueous catalyst precursor slurry.

As used herein, "source compounds" are compounds which contain and/or provide one or more of the metals for the mixed metal oxide catalyst composition. As used herein, "remaining elements" or "remaining elements in the catalyst" refers to those elements and the quantity of those elements represented by "A", "D", "E", "F" and "G" in the above formula which were not included in the first mixture. In one embodiment, some elements may be a part of both the first and second mixture. Further, as used herein, "remaining molybdenum" or "remaining molybdenum in the catalyst" refers to that quantity of molybdenum required in the finished catalyst which was not present (i.e. not included in the preparation of) in the precipitate slurry. Lastly, the sum of the quantities of molybdenum provided in the source compounds of molybdenum added in (ii) and (iii) is equal to the total quantity of molybdenum present in the catalyst.

In the catalyst preparation described herein, the source compounds of the remaining elements and of the remaining molybdenum which are combined with the precipitate slurry may be combined in any order or combination of such remaining elements and remaining molybdenum. In one embodiment, a mixture of the source compounds of the remaining elements and of the remaining molybdenum is combined with the precipitate slurry to form the aqueous catalyst precursor slurry. In another embodiment, (i) a mixture of the source compounds of the remaining elements is combined with the precipitate slurry, and (ii) source compounds of the remaining molybdenum are separately added to the precipitate slurry to form the aqueous catalyst precursor slurry. The order of addition is not critical. In another embodiment, source compounds of the remaining elements and of the remaining molybdenum are added individually (i.e. one at a time) to the precipitate slurry. In another embodiment, multiple (i.e. more than one) mixtures of source compounds of the remaining elements and of the remaining molybdenum, wherein each mixture contains one or more of the source compounds of the remaining elements or of the remaining molybdenum, are separately added (i.e. one mixture at a time or multiple mixtures added simultaneously) to the precipitate slurry to form the aqueous catalyst precursor slurry. In yet another embodiment, a mixture of source compounds of the remaining elements is combined with a source compound of molybdenum and the resulting mixture is then added to the precipitate slurry to form the catalyst precursor slurry. In yet another embodiment, the support is silica ($SiO_2$) and the silica is combined with a source compound for the remaining molybdenum prior to combining the remaining molybdenum with the precipitate slurry (i.e. the silica and a source compound for the remaining molybdenum are combined to form a mixture and then this mixture is added to the precipitate slurry, individually or in combination with one or more source compounds of the remaining elements).

In the catalyst preparation described herein, molybdenum is added both in the preparation of the precipitate slurry and in the preparation of the aqueous catalyst precursor slurry. On an atomic level, the minimum amount of molybdenum added to form the precipitate slurry is determined by the following relationship $$Mo=1.5(Bi+Ce)+0.5(Rb+Na+K+Cs)+(Ca)+1.5(\text{sum of the number of atoms of rare earth elements})+(Pb)+3(W)+1.5(Y)$$

Wherein in the above relationship "Mo" is the number of atoms of molybdenum to be added to the first mixture, and "Bi", "Ce", "Rb", "Na", "K", "Cs", "Ca", "Pb", "W" and "Y" is the number of atoms of bismuth, cerium, rubidium, sodium, potassium, cesium, calcium, lead, tungsten and yttrium, respectively, present in the first mixture.

Typically, the amount of molybdenum added to the first mixture to form the precipitate slurry is about 20 to 35% of the total molybdenum in the final catalyst. In one embodiment, a source compound for the remaining molybdenum present in the catalyst is added to the mixture of the source compounds of the remaining elements (i.e. the second mixture) prior to the combination of the mixture of the remaining elements with the precipitate slurry to form the to catalyst precursor slurry. In other embodiments, a source compound of molybdenum containing the remaining molybdenum present in the catalyst is added to the precipitate slurry either prior to, after or simultaneously with, the mixture of the source compounds of the remaining elements (i.e. the second mixture) in order to form the catalyst precursor slurry.

In the instant preparation, source compounds of Bi and Ce, and optionally one or more of Na, K, Rb, Cs, Ca, a rare earth element, Pb, W and Y, are combined in an aqueous solution to form a mixture. In one embodiment, bismuth nitrate and optionally other metal nitrates (i.e. nitrates of Na, K, Rb, Cs, Ca, a rare earth element, Pb, W and/or Y) are dissolved in an aqueous solution of ceric ammonium nitrate.

Added to the mixture comprising the bismuth and cerium (and optionally one or more of Na, K, Rb, Cs, Ca, a rare earth element, Pb, W and Y) is a source compound of molybdenum. In one embodiment this source compound of molybdenum is ammonium heptamolybdate dissolved in water. Upon the addition of the molybdenum source compound to the mixture comprising the bismuth and cerium, a reaction will occur which will result in a precipitate and the resulting mixture is the precipitate slurry.

The precipitate slurry is then combined with a mixture of source compound of the remaining elements of the catalyst and a source compound of molybdenum, to form the aqueous catalyst precursor slurry. The mixture of source compounds of the remaining elements and a source compound of molybdenum may be prepared by combining source compounds of the remaining elements in an aqueous solution (e.g. source compounds are combined in water) and then adding a source compound of molybdenum. In one embodiment this source compound of molybdenum is ammonium heptamolybdate dissolved in water. When combining the precipitate slurry with the remaining elements/molybdenum mixture, the order of addition is not important, i.e. the precipitate slurry may be added to the remaining elements/molybdenum mixture or the remaining elements/molybdenum mixture may be added to the precipitate slurry. The aqueous catalyst precursor slurry is maintained at an elevated temperature.

The amount of aqueous solvent in each of the above described aqueous mixtures and slurries may vary due to the solubilities of the source compounds combined to form the particular mixed metal oxide. The amount of aqueous solvent should at least be sufficient to yield a slurry or mixture of solids and liquids which is able to be stirred.

In any case, the source compounds are preferably combined and/or reacted by a protocol that comprises mixing the source compounds during the combination and/or reaction step. The particular mixing mechanism is not critical, and can include for example, mixing (e.g., to stirring or agitating) the components during the reaction by any effective method. Such methods include, for example, agitating the contents of the vessel, for example by shaking, tumbling or oscillating the component-containing vessel. Such methods also include, for example, stirring by using a stirring member located at least partially within the reaction vessel and a driving force coupled to the stirring member or to the reaction vessel to provide relative motion between the stirring member and the reaction vessel. The stirring member can be a shaft-driven and/or shaft-supported stirring member. The driving force can be directly coupled to the stirring member or can be indirectly coupled to the stirring member (e.g., via magnetic coupling). The mixing is generally preferably sufficient to mix the components to allow for efficient reaction between components of the reaction medium to form a more homogeneous reaction medium (e.g., and resulting in a more homogeneous mixed metal oxide precursor) as compared to an unmixed reaction. This results in more efficient consumption of starting materials and in a more uniform mixed metal oxide product. Mixing the precipitate slurry during the reaction step also causes the precipitate to form in solution rather than on the sides of the reaction vessel. More advantageously, having the precipitate form in solution allows for particle growth on all faces of the particle rather than the limited exposed faces when the growth occurs out from the reaction vessel wall.

A source compound of molybdenum may include molybdenum (VI) oxide ($MoO_3$), ammonium heptamolybdate or molybdic acid. The source compound of molybdenum may be introduced from any molybdenum oxide such as dioxide, trioxide, pentoxide or heptaoxide. However, it is preferred that a hydrolyzable or decomposable molybdenum salt be utilized as source compound of molybdenum.

Typical source compounds for bismuth, cerium and the remaining elements of the catalyst are nitrate salts of the metals. Such nitrate salts are readily available and easily soluble. A source compound of bismuth may include an oxide or a salt which upon calcination will yield the oxide. The water soluble salts which are easily dispersed but form stable oxides upon heat treating are preferred. In one embodiment the source compound of bismuth is bismuth nitrate, $Bi(NO_3)_3 \cdot 5H_2O$ A source compound of cerium may include an oxide or a salt which upon calcination will yield the oxide. The water soluble salts which are easily dispersed but form stable oxides upon heat treating are preferred. In one embodiment the source compound of cerium is ceric ammonium nitrate, $(NH_4)_2Ce(NO_3)_6$.

A source compound of iron may be obtained from any compound of iron which, upon calcination will result in the oxide. As with the other elements, water soluble salts are preferred for the ease with which they may be uniformly dispersed within the catalyst. Most preferred is ferric nitrate.

Source compounds for the remaining elements may be derived from any suitable source. For example, cobalt, nickel and magnesium may be introduced into the catalyst using nitrate salts. Additionally, magnesium may be introduced into the catalyst as an insoluble carbonate or hydroxide which upon heat treating results in an oxide. Phosphorus may be introduced in the catalyst as an alkaline metal salt or alkaline earth metal salt or the ammonium salt but is preferably introduced as phosphoric acid.

Source compounds for the alkali components of the catalyst may be introduced into the catalyst as an oxide or as a salt which upon calcination will yield the oxide.

Solvents, in addition to water, may be used to prepare the mixed metal oxides according to the invention include, but are not limited to, alcohols such as methanol, ethanol, propanol, diols (e.g. ethylene glycol, propylene glycol, etc.), organic acids such as acetic acid, as well as other polar solvents known in the art. The metal source compounds are at least partially soluble in the solvent.

As previously noted, the catalyst of the present invention may be used either supported or unsupported (i.e. the catalyst may comprise a support). Suitable supports are silica, alumina, zirconium, titania, or mixtures thereof. The point of addition of the support is not critical in the preparation of the catalyst. The support may be added anytime prior to the catalyst precursor slurry being dried. The support may be added at any time during or after the preparation of any mixture of elements, the precipitate slurry or the catalyst precursor slurry. Further the support need not be added in a single point or step (i.e. the support may be added at multiple points in the preparation. In one embodiment, the support is combined with the other ingredients during the preparation of the aqueous catalyst precursor slurry. In one embodiment, the support is added to the precipitate slurry (i.e. after the precipitate slurry is prepared). In one embodiment, the support is combined with the source compound of molybdenum prior to combining the source compound of molybdenum with source compounds of the remaining elements in the catalyst to form the "second mixture" referred to above.

The catalyst precursor slurry is dried and denitrified (i.e. the removal of nitrates) to yield the catalyst precursor. Preferably the catalyst precursor slurry is spray-dried at a temperature of between 110° C. and 350° C. dryer outlet temperature, preferably between 110° C. and 250° C., most preferably between 110° C. and 180° C. The denitrification temperature may range from 100° C. to 500° C., preferably 250° C. to 450° C.

Finally, the dried catalyst precursor is calcined. In one embodiment, the calcination is effected in air. In another embodiment, the calcination is effected in an inert atmosphere, such as nitrogen. Preferred calcination conditions include temperatures ranging from about 300° C. to about 700° C., more preferably from about 350° C. to about 650° C., and in some embodiments, the calcination may be at about 600° C.

The catalysts of the present invention may be prepared by any of the numerous methods of catalyst preparation which are known to those of skill in the art. In one embodiment, the catalyst components may be mixed with a support in the form of the slurry followed by drying or the catalyst components may be impregnated on silica or other supports.

Ammoxidation Process:

The catalysts of the instant invention are useful in ammoxidation processes for the conversion of an olefin selected from the group consisting of propylene, isobutylene or mixtures thereof, to acrylonitrile, methacrylonitrile and mixtures thereof, respectively, by reacting in the vapor phase at an elevated temperature and pressure said olefin with a molecular oxygen containing gas and ammonia in the presence of the catalyst. The catalysts of the instant invention are also useful for the ammoxidation of methanol to hydrogen cyanide and the ammoxidation of ethanol to acetonitrile. In one embodiment employing the catalysts described herein, methanol and/or ethanol can be co-fed to a process for the ammoxidation of propylene, isobutylene or mixtures thereof to acrylonitrile, methacrylonitrile or mixtures thereof, in order to increase the production of hydrogen cyanide and/or acetonitrile co-products resulting from such process.

Preferably, the ammoxidation reaction is performed in a fluid bed reactor although other types of reactors such as transport line reactors are envisioned. Fluid bed reactors, for the manufacture of acrylonitrile are well known in the prior art. For example, the reactor design set forth in U.S. Pat. No. 3,230,246, herein incorporated by reference, is suitable.

Conditions for the ammoxidation reaction to occur are also well known in the prior art as evidenced by U.S. Pat. Nos. 5,093,299; 4,863,891; 4,767,878 and 4,503,001; herein incorporated by reference. Typically, the ammoxidation process is performed by contacting propylene or isobutylene in the presence of ammonia and oxygen with a fluid bed catalyst at an elevated temperature to produce the acrylonitrile or methacrylonitrile. Any source of oxygen may be employed. For economic reasons, however, it is preferred to use air. The typical molar ratio of the oxygen to olefin in the feed should range from 0.5:1 to 4:1, preferably from 1:1 to 3:1.

The molar ratio of ammonia to olefin in the feed in the reaction may vary from between 0.5:1 to 2:1. There is really no upper limit for the ammonia-olefin ratio, but there is generally no reason to exceed a ratio of 2:1 for economic reasons. Suitable feed ratios for use with the catalyst of the instant invention for the production of acrylonitrile from propylene are an ammonia to propylene ratio in the range of 0.9:1 to 1.3:1, and air to propylene ratio of 8.0:1 to 12.0:1. The catalyst of the instant invention is able to provide high yields of acrylonitrile at relatively low ammonia to propylene feed ratios of about 1:1 to about 1.05:1. These "low ammonia conditions" help to reduce unreacted ammonia in the reactor effluent, a condition known as "ammonia breakthrough", which subsequently helps to reduce process wastes. Specifically, unreacted ammonia must be removed from the reactor effluent prior to the recovery of the acrylonitrile. Unreacted ammonia is typically removed by contacting the reactor effluent with sulfuric acid to yield ammonium sulfate or by contacting the reactor effluent with acrylic acid to yield ammonium acrylate, which in both cases results in a process waste stream to be treated and/or disposed.

The reaction is carried out at a temperature of between the ranges of about 260° to 600° C., preferred ranges being 310° to 500° C., especially preferred being 350° to 480° C. The contact time, although not critical, is generally in the range of 0.1 to 50 seconds, with preference being to a contact time of 1 to 15 seconds.

The products of reaction may be recovered and purified by any of the methods known to those skilled in the art. One such method involves scrubbing the effluent gases from the reactor with cold water or an appropriate solvent to remove the products of the reaction and then purifying the reaction product by distillation.

The primary utility of the catalyst prepared by the process of the instant invention is for the ammoxidation of propylene to acrylonitrile. Other utilities include the ammoxidation of propane to acrylonitrile and the ammoxidation of ethanol to acetonitrile. The catalyst prepared by the process of the instant invention may also be used for the oxidation of propylene to acrylic acid. Such processes are typically two stage processes, wherein propylene is converted in the presence of a catalyst to primarily acrolein in the first stage and the acrolein is converted in the presence of a catalyst to primarily acrylic acid in the second stage. The catalyst described herein is suitable for use in the first stage for the oxidation of propylene to acrolein.

Specific Embodiments

In order to illustrate the instant invention, catalyst prepared in accordance with the instant invention were evaluated and compared under similar reaction conditions to similar catalysts prepared by prior art methods outside the scope of the instant invention. These examples are provided for illustrative purposes only.

Catalysts having the composition of $Cs_{0.1}K_{0.1}Ni_5Mg_2Na_{0.05}Fe_{1.8}Bi_{0.45}Ce_{1.1}Mo_{12.55}O_{50.35}$ +45 wt % $SiO_2$ were prepared by various preparation methods as described below and tested in a bench scale reactor for the ammoxidation of propylene to acrylonitrile. All testing was conducted in a 40 cc fluid bed reactor. Propylene was feed into the reactor at a rate of 0.06 WWH (i.e. weight of propylene/weight of catalyst/hour). Pressure inside the reactor was maintained at 10 psig. Reaction temperature was 430° C. After a stabilization period of ~20 hours or more, samples of reaction products were collected. Reactor effluent was collected in bubble-type scrubbers containing cold HCl solution. Off-gas rate was measured with soap film meter, and the off-gas composition was determined at the end of the run with the aid of gas chromatograph fitted with a split column gas analyzer. At the end of the recovery run, the entire scrubber liquid was diluted to approximately 200 gms with distilled water. A weighted amount of 2-butanone was used as internal standard in a ~50 gram aliquot of the dilute solution. A 2 µl sample was analyzed in a GC fitted with a flame ionization detector and a Carbowax column. The amount of $NH_3$ was determined by titrating the free HCl excess with NaOH solution.

COMPARATIVE EXAMPLE C1

Conventional Method

Reaction mixture A was prepared by heating 224 ml of deionized water to 65° C. and then adding with stirring over 30 minutes ammonium heptamolybdate (203.75 g) to form a clear colorless solution. Silica sol (625 g, 32.5 wt % silica) was then added with stirring.

Reaction mixture B was prepared by heating 30 ml of deionized water to 55° C. and then adding with stirring Fe$(NO_3)_3.9H_2O$ (66.9 g), Ni$(NO_3)_2.6H_2O$ (133.7 g), Mg$(NO_3)_2.6H_2O$ (47.2 g), Bi$(NO_3)_3.5H_2O$ (20.1 g), CsNO$_3$ (1.79 g), KNO$_3$ (0.93 g), and NaNO$_3$ (0.39 g). Next, 110.0 g of 50 wt % aqueous $(NH_4)_2Ce(NO_3)_6$ solution was added with stirring.

Reaction mixture B was then added to reaction mixture A with stirring to from the catalyst precursor slurry. The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/140° C. The resulting powder was denitrified by heat treating for 3 hours in air at 290° C., followed by an additional 3 hours at 425° C. The powder was then calcined in air at 560° C. for 3 hours. The resulting calcined powder was then tested as a propylene ammoxidation catalyst in a 40 cc microreactor. Testing results are shown in Table 1.

COMPARATIVE EXAMPLE C2

Prepared According to U.S. Pat. No. 4,212,766 (i.e. no Bi—Ce—Mo Precipitate Slurry Formed as a Separate Step Reaction mixture A was prepared by heating 233 ml of deionized water to 65° C. and then adding with stirring over 30 minutes ammonium heptamolybdate (212.1 g) to form a clear colorless solution. Silica sol (692 g, 32.5 wt % silica) was then added with stirring.

Reaction mixture B was prepared by heating 33 ml of deionized water to 55° C. and then adding sequentially with stirring Fe(NO$_3$)$_3$.9H$_2$O (73.6 g), Ni(NO$_3$)$_2$.6H$_2$O (147.1 g), Mg(NO$_3$)$_2$.6H$_2$O (51.9 g), CsNO$_3$ (1.97 g), KNO$_3$ (1.02 g), NaNO$_3$ (0.43 g), and 122.0 g of 50 wt % aqueous (NH$_4$)$_2$Ce(NO$_3$)$_6$ solution.

Reaction mixture C was prepared by heating 152 ml of deionized water to 65° C. and then adding with stirring over 30 minutes ammonium heptamolybdate (12.1 g) to form a clear colorless solution.

Reaction mixture D was prepared by dissolving Bi(NO$_3$)$_3$.5H$_2$O (22.1 g) in 160 g of 10 wt % aqueous HNO$_3$ solution.

Reaction mixture E was prepared by adding with stirring reaction mixture B to reaction mixture A.

Reaction mixture F was prepared by adding reaction mixture D to reaction mixture C. This resulted in precipitation of a colorless solid. Stirring was continued for 15 minutes while the temperature was maintained in the 50-55° C. range.

Reaction mixture F was then added to reaction mixture E to form the final catalyst precursor slurry.

The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/140° C. The resulting powder was denitrified by heat treating for 3 hours in air at 290° C., followed by an additional 3 hours at 425° C. The powder was then calcined in air at 560° C. for 3 hours. The resulting calcined powder was then tested as a propylene ammoxidation catalyst in a 40 cc microreactor. Testing results are shown in Table 1.

EXAMPLE 1

Prepared in Accordance with the Invention

Reaction mixture A was prepared by heating 198 ml of deionized water to 65° C. and then adding with stirring over 30 minutes ammonium heptamolybdate (180.4 g) to form a clear colorless solution. Silica sol (692 g, 32.5 wt % silica) was then added with stirring.

Reaction mixture B was prepared by heating 33 ml of deionized water to 55° C. and then adding with stirring Fe(NO$_3$)$_3$.9H$_2$O (73.6 g), Ni(NO$_3$)$_2$.6H$_2$O (147.1 g), and Mg(NO$_3$)$_2$.6H$_2$O (51.9 g).

Reaction mixture C was prepared by heating 48 ml of deionized water to 65° C. and then adding with stirring over 30 minutes ammonium heptamolybdate (43.75 g) to form a clear colorless solution.

Reaction mixture D was prepared by (i) heating 122.0 g of 50 wt % aqueous (NH$_4$)$_2$Ce(NO$_3$)$_6$ solution to 55° C., and (ii) while the solution was stirring and heating, sequentially adding Bi(NO$_3$)$_3$.5H$_2$O (22.1 g), CsNO$_3$ (1.97 g), KNO$_3$ (1.02 g), and NaNO$_3$ (0.43 g), resulting in a clear orange solution.

Reaction mixture E was prepared by adding with stirring reaction mixture B to reaction mixture A.

Reaction mixture F was prepared by adding reaction mixture C to reaction mixture D. This resulted in precipitation of an orange solid. The resulting mixture was the precipitate slurry. Stirring of Reaction mixture F was continued for 15 minutes while the temperature was maintained in the 50-55° C. range.

Reaction mixture F was then added to reaction mixture E to form the final catalyst precursor slurry.

The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/140° C. The resulting powder was denitrified by heat treating for 3 hours in air at 290° C., followed by an additional 3 hours at 425° C. The powder was then calcined in air at 560° C. for 3 hours. The resulting calcined powder was then tested as a propylene ammoxidation catalyst in a 40 cc microreactor. Testing results are shown in Table 1.

EXAMPLE 2

Prepared in Accordance with the Invention

Reaction mixture A was prepared by heating 198 ml of deionized water to 65° C. and then adding with stirring over 30 minutes ammonium heptamolybdate (180.4 g) to form a clear colorless solution.

Reaction mixture B was prepared by heating 33 ml of deionized water to 55° C. and then adding with stirring Fe(NO$_3$)$_3$.9H$_2$O (73.6 g), Ni(NO$_3$)$_2$.6H$_2$O (147.1 g), and Mg(NO$_3$)$_2$.6H$_2$O (51.9 g).

Reaction mixture C was prepared by heating 48 ml of deionized water to 65° C. and then adding with stirring over 30 minutes ammonium heptamolybdate (43.75 g) to form a clear colorless solution.

Reaction mixture D was prepared by (i) heating 122.0 g of 50 wt % aqueous (NH$_4$)$_2$Ce(NO$_3$)$_6$ solution to 55° C., (ii) while the solution was stirring and heating, sequentially adding Bi(NO$_3$)$_3$.5H$_2$O (22.1 g), CsNO$_3$ (1.97 g), KNO$_3$ (1.02 g), and NaNO$_3$ (0.43 g), resulting in a clear orange solution.

Reaction mixture E was prepared by adding with stirring reaction mixture B to reaction mixture A.

Reaction mixture F was prepared by (i) adding reaction mixture C to reaction mixture D, which resulted in precipitation of an orange solid (this resulting mixture was the precipitate slurry), (ii) stirring of the precipitate slurry was continued for 15 minutes while the temperature was maintained in the 50-55° C. range, and (iii) adding with stirring silica sol (692 g, 32.5 wt % silica).

Reaction mixture E was then added to reaction mixture F to form the final catalyst precursor slurry.

The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/140° C. The resulting powder was denitrified by heat treating for 3 hours in air at 290° C., followed by an additional 3 hours at 425° C. The powder was then calcined in air at 560° C. for 3 hours. The resulting calcined powder was then tested as a propylene ammoxidation catalyst in a 40 cc microreactor. Testing results are shown in Table 1.

TABLE 1

Comparison of Cs$_{0.1}$K$_{0.1}$Ni$_5$Mg$_2$Na$_{0.05}$Fe$_{1.8}$Bi$_{0.45}$Ce$_{1.1}$Mo$_{12.55}$O$_{50.35}$ + 45 wt % SiO2 Catalyst Prepared by Different Methods

| Example | HOS | Total C$_3^=$ Conv. | Conv. to AN | Conv. to HCN | Conv. to AN and HCN |
|---------|-----|---------------------|-------------|--------------|---------------------|
| C1      | 160 | 96.3                | 80.4        | 5.2          | 85.6                |
| C2      | 97  | 99.0                | 81.1        | 4.5          | 85.6                |

TABLE 1-continued

Comparison of $Cs_{0.1}K_{0.1}Ni_5Mg_2Na_{0.05}Fe_{1.8}Bi_{0.45}Ce_{1.1}Mo_{12.55}O_{50.35}$ + 45 wt % SiO2 Catalyst Prepared by Different Methods

| Example | HOS | Total $C_3^=$ Conv. | Conv. to AN | Conv. to HCN | Conv. to AN and HCN |
|---------|-----|---------------------|-------------|--------------|---------------------|
| 1 | 150 | 98.6 | 80.9 | 5.6 | 86.6 |
| 2 | 161 | 98.8 | 81.9 | 5.8 | 87.7 |

Notes:
1. All test catalyst compositions contained 55 wt % active phase and 45 wt % 22 nm low Na SiO₂.
2. "HOS" is the "hours on stream", i.e. the amount of time the catalyst was evaluated under test conditions.
3. "Total $C_3^=$ Conv." is the mole percent per pass conversion of propylene to all products.
4. "Conv. to AN" is the mole percent per pass conversion of propylene to acrylonitrile.
5. "Conv. to HCN" is the mole percent per pass conversion of propylene to hydrogen cyanide.
6. "Conv. to AN and HCN" is the total mole percent per pass conversion of propylene to acrylonitrile and hydrogen cyanide.

As can be seen from Table 1, the catalyst compositions, prepared by the method of the instant invention, exhibit higher conversions to acrylonitrile and HCN when propylene was ammoxidized over such catalyst at elevated temperatures in the presence of ammonia and air compared to identical catalysts prepared by methods falling outside the scope of the instant invention.

In order to further illustrate the instant invention, catalyst with compositions within the scope of the instant invention (Examples 3 through 7) were prepared and were evaluated and compared under similar reaction conditions to similar catalysts with compositions outside the scope of the instant invention (Comparative Examples C3 through C7). These examples are provided for illustrative purposes only.

COMPARATIVE EXAMPLE 3

C-49MC Acrylonitrile Catalyst

Testing results and other data are shown in Tables 2 for C-49MC Acrylonitrile Catalyst. "Catalyst C-49MC" is the product designation for commercial catalyst manufactured and sold by INEOS USA LLC. The composition of Catalyst C-49MC is a trade secret of INEOS USA LLC. "C-49MC" is a trademark of INEOS USA LLC.

COMPARATIVE EXAMPLE C4

$Ni_{7.5}Mg_3Fe_{1.8}Rb_{0.12}Cr_{0.1}Bi_{0.45}Ce_{1.1}Mo_{15.85}O_{63.835}$+
50 wt % 27 ppm Na, 39 nm $SiO_2$ Reaction mixture A was prepared by heating 225.1 ml of deionized water to 65° C. and then adding with stirring over 30 minutes ammonium heptamolybdate (204.6 g) to form a clear colorless solution. Silica sol (27 ppm Na, 39 nm avg. particle size, 595.2 g, 42 wt % silica) was then added with stirring.
Reaction mixture B was prepared by heating 32.2 ml of deionized water to 55° C. and then adding with stirring Fe(NO₃)₃.9H₂O (53.2 g), Ni(NO₃)₂.6H₂0 (159.5 g), Mg(NO₃)₂.6H₂O (56.2 g), Bi(NO₃)₃.5H₂O (16 g), Cr(NO₃)₃.9H₂0 (2.9 g) and RbNO₃ (1.3 g).
88.2 g of 50 wt % aqueous (NH₄)₂Ce(NO₃)₆ solution was added to solution B followed by adding this resulting mixture to solution A with mixing at ~55° C. for one hour followed by cooling to 40° C. The resulting catalyst slurry was then homogenized in a blender for 3 minutes at 5000 rpm. The slurry was then spray dried in a spray dryer at an inlet/outlet temperature of 325/140° C. The resulting powder was denitrified by heat treating 3 hours in air at 290° C., 3 hours in air at 425° C. and then calcined in air at 560° C. for 3 hours. The resulting calcined powder was then tested as a propylene ammoxidation catalyst. Testing results are shown in Table 2.

COMPARATIVE EXAMPLE C5

$Ni_{7.5}Mg_3Fe_{1.8}Rb_{0.12}Cr_{0.1}Bi_{0.45}Ce_{1.1}Mo_{15.85}O_{63.835}$+
50 wt % $SiO_2$

Reaction mixture A was prepared by heating 191.1 ml of deionized water to 65° C. and then adding with stirring over 30 minutes ammonium heptamolybdate (173.8 g) to form a clear colorless solution. Silica sol (27 ppm Na, 39 nm avg. particle size, 595.2 g, 42 wt % silica) was then added with stirring.
Reaction mixture B was prepared by heating 32.1 ml of deionized water to 55° C. and then adding with stirring Fe(NO₃)₃.9H₂O (53.2 g), Ni(NO₃)₂.6H₂0 (159.5 g), Mg(NO₃)₂.6H₂O (56.2 g) and Cr(NO₃)₃.9H₂0 (2.9 g).
Reaction mixture C was prepared by heating 33.9 ml of deionized water to 65° C. and then adding with stirring over 30 minutes ammonium heptamolybdate (30.8 g) to form a clear colorless solution.
Reaction mixture D was prepared by (i) heating 88.2 g of 50 wt % aqueous (NH₄)₂Ce(NO₃)₆ solution to 55° C., and (ii) while the solution was stirring and heating, sequentially adding Bi(NO₃)₃.5H₂O (16 g) and RbNO₃ (1.3 g) resulting in a clear orange solution.
Reaction mixture E was prepared by adding with stirring reaction mixture B to reaction mixture A.
Reaction mixture F was prepared by adding reaction mixture C to reaction mixture D. This resulted in precipitation of an orange solid. The resulting mixture was the precipitate slurry. Stirring of Reaction mixture F was continued for 15 minutes while the temperature was maintained in the 50-55° C. range.
Reaction mixture F was then added to reaction mixture E to form the final catalyst precursor slurry.
The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/140° C. The resulting powder was denitrified by heat treating 3 hours in air at 290° C., 3 hours in air at 425° C. and then calcined in air at 560° C. for 3 hours. The resulting calcined powder was then tested as a propylene ammoxidation catalyst. Testing results are shown in Table 2.

COMPARATIVE EXAMPLE C6

$Ni_5Mg_2Fe_{1.8}Rb_{0.12}Cr_{0.1}Bi_{0.45}Ce_{1.1}Mo_{12.35}O_{49.835}$+
50 $SiO_2$

Reaction mixture A was prepared by heating 1619.7 ml of deionized water to 65° C. and then adding with stirring over 30 minutes ammonium heptamolybdate (1472.5 g) to form a clear colorless solution. Silica sol (27 ppm Na, 39 nm avg. particle size, 5357.1 g, 42 wt % silica) was then added with stirring.
Reaction mixture B was prepared by heating 276.2 ml of deionized water to 55° C. and then adding with stirring Fe(NO₃)₃.9H₂O (608.6 g), Ni(NO₃)₂.6H₂0 (1216.8 g), Mg(NO₃)₂.6H₂O (429.2 g) and Cr(NO₃)₃.9H₂0 (33.5 g).
Reaction mixture C was prepared by heating 387.7 ml of deionized water to 65° C. and then adding with stirring over 30 minutes ammonium heptamolybdate (352.4 g) to form a clear colorless solution.

Reaction mixture D was prepared by (i) heating 1009.4 g of 50 wt % aqueous $(NH_4)_2Ce(NO_3)_6$ solution to 55° C., and (ii) while the solution was stirring and heating, sequentially adding $Bi(NO_3)_3.5H_2O$ (182.7 g) and $RbNO_3$ (14.8 g) resulting in a clear orange solution.

Reaction mixture E was prepared by adding with stirring reaction mixture B to reaction mixture A.

Reaction mixture F was prepared by adding reaction mixture C to reaction mixture D. This resulted in precipitation of an orange solid. The resulting mixture was the precipitate slurry. Stirring of Reaction mixture F was continued for 15 minutes while the temperature was maintained in the 50-55° C. range.

Reaction mixture F was then added to reaction mixture E to form the final catalyst precursor slurry.

The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/140° C. The resulting powder was denitrified by heat treating 3 hours in air at 290° C., 3 hours in air at 425° C. and then calcined in air at 560° C. for 3 hours. The resulting calcined powder was then tested as a propylene ammoxidation catalyst. Testing results are shown in Table 2.

COMPARATIVE EXAMPLE C7

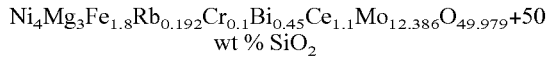
$Ni_4Mg_3Fe_{1.8}Rb_{0.192}Cr_{0.1}Bi_{0.45}Ce_{1.1}Mo_{12.386}O_{49.979}$+50 wt % $SiO_2$ Reaction mixture A was prepared by heating 181.5 ml of deionized water to 65° C. and then adding with stirring over 30 minutes ammonium heptamolybdate (165 g) to form a clear colorless solution. Silica sol (90 ppm Na, 39.2 nm avg. particle size, 606.8 g, 41.2 wt % silica) was then added with stirring.

Reaction mixture B was prepared by heating 30.7 ml of deionized water to 55° C. and then adding with stirring $Fe(NO_3)_3.9H_2O$ (68.2 g), $Ni(NO_3)_2.6H_2O$ (109.1 g), $Mg(NO_3)_2.6H_2O$ (72.1 g) and $Cr(NO_3)_3.9H_2O$ (3.8 g).

Reaction mixture C was prepared by heating 44.1 ml of deionized water to 65° C. and then adding with stirring over 30 minutes ammonium heptamolybdate (40.1 g) to form a clear colorless solution.

Reaction mixture D was prepared by (i) heating 113.1 g of 50 wt % aqueous $(NH_4)_2Ce(NO_3)_6$ solution to 55° C., and (ii) while the solution was stirring and heating, sequentially adding $Bi(NO_3)_3.5H_2O$ (20.5 g) and $RbNO_3$ (2.7 g) resulting in a clear orange solution.

Reaction mixture E was prepared by adding with stirring reaction mixture B to reaction mixture A.

Reaction mixture F was prepared by adding reaction mixture C to reaction mixture D. This resulted in precipitation of an orange solid. The resulting mixture was the precipitate slurry. Stirring of Reaction mixture F was continued for 15 minutes while the temperature was maintained in the 50-55° C. range.

Reaction mixture F was then added to reaction mixture E to form the final catalyst precursor slurry.

The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/140° C. The resulting powder was denitrified by heat treating 3 hours in air at 290° C., 3 hours in air at 425° C. and then calcined in air at 560° C. for 3 hours. The resulting calcined powder was then tested as a propylene ammoxidation catalyst. Testing results are shown in Table 2.

EXAMPLE 3

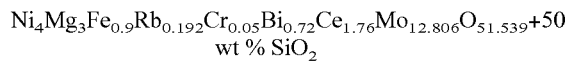
$Ni_4Mg_3Fe_{0.9}Rb_{0.192}Cr_{0.05}Bi_{0.72}Ce_{1.76}Mo_{12.806}O_{51.539}$+50 wt % $SiO_2$ Reaction mixture A was prepared by heating 154.5 ml of deionized water to 65° C. and then adding with stirring over 30 minutes ammonium heptamolybdate (140.4 g) to form a clear colorless solution. Silica sol (27 ppm Na, 39 nm avg. particle size, 595.2 g, 42 wt % silica) was then added with stirring.

Reaction mixture B was prepared by heating 26.5 ml of deionized water to 55° C. and then adding with stirring $Fe(NO_3)_3.9H_2O$ (32.2 g), $Ni(NO_3)_2.6H_2O$ (102.9 g), $Mg(NO_3)_2.6H_2O$ (68 g) and $Cr(NO_3)_3.9H_2O$ (1.8 g).

Reaction mixture C was prepared by heating 65.5 ml of deionized water to 65° C. and then adding with stirring over 30 minutes ammonium heptamolybdate (59.6 g) to form a clear colorless solution.

Reaction mixture D was prepared by (i) heating 170.6 g of 50 wt % aqueous $(NH_4)_2Ce(NO_3)_6$ solution to 55° C., and (ii). while the solution was stirring and heating, sequentially adding $Bi(NO_3)_3.5H_2O$ (30.9 g) and $RbNO_3$ (2.5 g) resulting in a clear orange solution.

Reaction mixture E was prepared by adding with stirring reaction mixture B to reaction mixture A.

Reaction mixture F was prepared by adding reaction mixture C to reaction mixture D. This resulted in precipitation of an orange solid. The resulting mixture was the precipitate slurry. Stirring of Reaction mixture F was continued for 15 minutes while the temperature was maintained in the 50-55° C. range.

Reaction mixture F was then added to reaction mixture E to form the final catalyst precursor slurry.

The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/140° C. The resulting powder was denitrified by heat treating 3 hours in air at 290° C., 3 hours in air at 425° C. and then calcined in air at 560° C. for 3 hours. The resulting calcined powder was then tested as a propylene ammoxidation catalyst. Testing results are shown in Table 2.

EXAMPLE 4

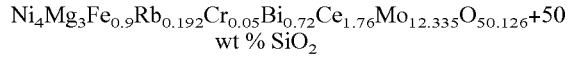
$Ni_4Mg_3Fe_{0.9}Rb_{0.192}Cr_{0.05}Bi_{0.72}Ce_{1.76}Mo_{12.335}O_{50.126}$+50 wt % $SiO_2$ Reaction mixture A was prepared by heating 149.9 ml of deionized water to 65° C. and then adding with stirring over 30 minutes ammonium heptamolybdate (136.3 g) to form a clear colorless solution. Silica sol (27 ppm Na, 39 nm avg. particle size, 595.2 g, 42 wt % silica) was then added with stirring.

Reaction mixture B was prepared by heating 27.1 ml of deionized water to 55° C. and then adding with stirring $Fe(NO_3)_3.9H_2O$ (32.9 g), $Ni(NO_3)_2.6H_2O$ (105.4 g), $Mg(NO_3)_2.6H_2O$ (69.7 g) and $Cr(NO_3)_3.9H_2O$ (1.8 g).

Reaction mixture C was prepared by heating 67.1 ml of deionized water to 65° C. and then adding with stirring over 30 minutes ammonium heptamolybdate (61 g) to form a clear colorless solution.

Reaction mixture D was prepared by (i) heating 174.8 g of 50 wt % aqueous $(NH_4)_2Ce(NO_3)_6$ solution to 55° C., and (ii) while the solution was stirring and heating, sequentially adding $Bi(NO_3)_3.5H_2O$ (31.6 g) and $RbNO_3$ (2.6 g) resulting in a clear orange solution.

Reaction mixture E was prepared by adding with stirring reaction mixture B to reaction mixture A.

Reaction mixture F was prepared by adding reaction mixture C to reaction mixture D. This resulted in precipitation of an orange solid. The resulting mixture was the precipitate slurry. Stirring of Reaction mixture F was continued for 15 minutes while the temperature was maintained in the 50-55° C. range.

Reaction mixture F was then added to reaction mixture E to form the final catalyst precursor slurry.

The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/140° C. The resulting powder was denitrified by heat treating 3 hours in air at 290° C., 3 hours in air at 425° C. and then calcined in air at 560° C. for 3 hours. The resulting calcined powder was then tested as a propylene ammoxidation catalyst. Testing results are shown in Table 2.

EXAMPLE 5

$$Ni_{4.26}Mg_{3.195}Fe_{0.9}Rb_{0.192}Cr_{0.05}Bi_{0.72}Ce_{1.76}Mo_{12.806}O_{51.994} + 50\text{ wt }\%\text{ SiO}_2$$

Reaction mixture A was prepared by heating 152.9 ml of deionized water to 65° C. and then adding with stirring over 30 minutes ammonium heptamolybdate (139 g) to form a clear colorless solution. Silica sol (27 ppm Na, 39 nm avg. particle size, 595.2 g, 42 wt % silica) was then added with stirring.

Reaction mixture B was prepared by heating 27.4 ml of deionized water to 55° C. and then adding with stirring $Fe(NO_3)_3.9H_2O$ (31.8 g), $Ni(NO_3)_2.6H_2O$ (108.5 g), $Mg(NO_3)_2.6H_2O$ (71.7 g) and $Cr(NO_3)_3.9H_2O$ (1.8 g).

Reaction mixture C was prepared by heating 64.9 ml of deionized water to 65° C. and then adding with stirring over 30 minutes ammonium heptamolybdate (59 g) to form a clear colorless solution.

Reaction mixture D was prepared by (i) heating 169 g of 50 wt % aqueous $(NH_4)_2Ce(NO_3)_6$ solution to 55° C., and (ii) while the solution was stirring and heating, sequentially adding $Bi(NO_3)_3.5H_2O$ (30.6 g) and $RbNO_3$ (2.5 g) resulting in a clear orange solution.

Reaction mixture E was prepared by adding with stirring reaction mixture B to reaction mixture A.

Reaction mixture F was prepared by adding reaction mixture C to reaction mixture D. This resulted in precipitation of an orange solid. The resulting mixture was the precipitate slurry. Stirring of Reaction mixture F was continued for 15 minutes while the temperature was maintained in the 50-55° C. range.

Reaction mixture F was then added to reaction mixture E to form the final catalyst precursor slurry.

The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/140° C. The resulting powder was denitrified by heat treating 3 hours in air at 290° C., 3 hours in air at 425° C. and then calcined in air at 560° C. for 3 hours. The resulting calcined powder was then tested as a propylene ammoxidation catalyst. Testing results are shown in Table 2.

EXAMPLE 6

$$Ni_4Mg_3Fe_{0.9}Rb_{0.192}Cr_{0.05}Bi_{0.72}Ce_{1.76}Mo_{12.502}O_{50.627} + 50\text{ wt }\%\text{ SiO}_2$$

Reaction mixture A was prepared by heating 1363.6 ml of deionized water to 65° C. and then adding with stirring over 30 minutes ammonium heptamolybdate (1239.6 g) to form a clear colorless solution. Silica sol (90 ppm Na, 39 nm avg. particle size, 5461.2 g, 41.2 wt % silica) was then added with stirring.

Reaction mixture B was prepared by heating 241.9 ml of deionized water to 55° C. and then adding with stirring $Fe(NO_3)_3.9H_2O$ (293.9 g), $Ni(NO_3)_2.6H_2O$ (940.2 g), $Mg(NO_3)_2.6H_2O$ (621.8 g) and $Cr(NO_3)_3.9H_2O$ (16.2 g).

Reaction mixture C was prepared by heating 599.1 ml of deionized water to 65° C. and then adding with stirring over 30 minutes ammonium heptamolybdate (544.6 g) to form a clear colorless solution.

Reaction mixture D was prepared by (i) heating 1559.9 g of 50 wt % aqueous $(NH_4)_2Ce(NO_3)_6$ solution to 55° C., and (ii) while the solution was stirring and heating, sequentially adding $Bi(NO_3)_3.5H_2O$ (282.3 g) and $RbNO_3$ (22.9 g) resulting in a clear orange solution.

Reaction mixture E was prepared by adding with stirring reaction mixture B to reaction mixture A.

Reaction mixture F was prepared by adding reaction mixture C to reaction mixture D. This resulted in precipitation of an orange solid. The resulting mixture was the precipitate slurry. Stirring of Reaction mixture F was continued for 15 minutes while the temperature was maintained in the 50-55° C. range.

Reaction mixture F was then added to reaction mixture E to form the final catalyst precursor slurry.

The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/145° C. The resulting powder was denitrified by heat treating 3 hours in air at 290° C., 3 hours in air at 425° C. and then calcined in air at 560° C. for 3 hours. The resulting calcined powder was then tested as a propylene ammoxidation catalyst. Testing results are shown in Table 2.

EXAMPLE 7

$$Ni_4Mg_3Fe_{0.9}Rb_{0.192}Cr_{0.05}Bi_{0.72}Ce_{1.76}Mo_{12.806}O_{51.539} + 50\text{ wt }\%,\ 22\text{ nm SiO}_2$$

Reaction mixture A was prepared by heating 154.4 ml of deionized water to 65° C. and then adding with stirring over 30 minutes ammonium heptamolybdate (140.4 g) to form a clear colorless solution. Silica sol (568 ppm Na, 22 nm avg. particle size, 625 g, 40 wt % silica) was then added with stirring.

Reaction mixture B was prepared by heating 26.5 ml of deionized water to 55° C. and then adding with stirring $Fe(NO_3)_3.9H_2O$ (32.2 g), $Ni(NO_3)_2.6H_2O$ (102.9 g), $Mg(NO_3)_2.6H_2O$ (68 g) and $Cr(NO_3)_3.9H_2O$ (1.8 g).

Reaction mixture C was prepared by heating 65.5 ml of deionized water to 65° C. and then adding with stirring over 30 minutes ammonium heptamolybdate (59.6 g) to form a clear colorless solution.

Reaction mixture D was prepared by (i) heating 170.6 g of 50 wt % aqueous $(NH_4)_2Ce(NO_3)_6$ solution to 55° C., and (ii) while the solution was stirring and heating, sequentially adding $Bi(NO_3)_3 \cdot 5H_2O$ (30.9 g) and $RbNO_3$ (2.5 g) resulting in a clear orange solution.

Reaction mixture E was prepared by adding with stirring reaction mixture B to reaction mixture A.

Reaction mixture F was prepared by adding reaction mixture C to reaction mixture D. This resulted in precipitation of an orange solid. The resulting mixture was the precipitate slurry. Stirring of Reaction mixture F was continued for 15 minutes while the temperature was maintained in the 50-55° C. range.

Reaction mixture F was then added to reaction mixture E to form the final catalyst precursor slurry.

The catalyst precursor slurry was allowed to stir for one hour while it cooled to approximately 40° C. It was then homogenized in a blender for 3 minutes at 5000 rpm. The slurry was then spray dried in a spray dryer at an inlet/outlet temperature of 325/140° C. The resulting powder was denitrified by heat treating 3 hours in air at 290° C., 3 hours in air at 425° C. and then calcined in air at 560° C. for 3 hours. The resulting calcined powder was then tested as a propylene ammoxidation catalyst. Testing results are shown in Table 2.

TABLE 2

| Ex. No. | Catalyst | X/Y Ratio | HOS | % $C_3^=$ Conv | % AN Yield | % AN Sel | % —CN Yield |
|---|---|---|---|---|---|---|---|
| C3 | Catalyst C49MC | 0.35 | | | | | 87.0 |
| C4 | $Ni_{7.5}Mg_3Fe_{1.8}Rb_{0.12}Cr_{0.1}Bi_{0.45}Ce_{1.1}Mo_{15.85}O_{63.835}$ + 50 wt % 27 ppm Na, 39 nm $SiO_2$ | 0.32 | 137 | 97.2 | 79.6 | 81.8 | 86.7 |
| C5 | $Ni_{7.5}Mg_3Fe_{1.8}Rb_{0.12}Cr_{0.1}Bi_{0.45}Ce_{1.1}Mo_{15.85}O_{63.835}$ + 50 wt % 27 ppm Na, 39 nm $SiO_2$ | 0.32 | 138 | 98.4 | 79.4 | 80.7 | 86.5 |
| C6 | $Ni_5Mg_2Fe_{1.8}Rb_{0.12}Cr_{0.1}Bi_{0.45}Ce_{1.1}Mo_{12.35}O_{49.835}$ + 50 wt % 27 ppm Na, 39 nm $SiO_2$ | 0.45 | 44 | 99.0 | 81.7 | 82.6 | 88.9 |
| C7 | $Ni_4Mg_3Fe_{1.8}Rb_{0.192}Cr_{0.1}Bi_{0.45}Ce_{1.1}Mo_{12.386}O_{49.979}$ + 50 wt % 90 ppm Na, 39.2 nm $SiO_2$ | 0.51 | 142 | 99.0 | 83.6 | 84.5 | 89.9 |
| 3 | $Ni_4Mg_3Fe_{0.9}Rb_{0.192}Cr_{0.05}Bi_{0.72}Ce_{1.76}Mo_{12.806}O_{51.539}$ + 50 wt % 27 ppm Na, 39 nm $SiO_2$ | 0.92 | 136 | 98.1 | 84.0 | 85.6 | 90.3 |
| 4 | $Ni_4Mg_3Fe_{0.9}Rb_{0.192}Cr_{0.05}Bi_{0.72}Ce_{1.76}Mo_{12.335}O_{50.126}$ + 50 wt % 27 ppm Na, 39 nm $SiO_2$ | 0.93 | 113 | 99.7 | 82.2 | 82.5 | 89.1 |
| 5 | $Ni_{4.26}Mg_{3.195}Fe_{0.9}Rb_{0.192}Cr_{0.05}Bi_{0.72}Ce_{1.76}Mo_{12.806}O_{51.994}$ + 50 wt % 27 ppm Na, 39 nm $SiO_2$ | 0.85 | 142 | 98.6 | 82.4 | 83.6 | 89.2 |
| 6 | $Ni_4Mg_3Fe_{0.9}Rb_{0.192}Cr_{0.05}Bi_{0.72}Ce_{1.76}Mo_{12.50}O_{50.627}$ + 50 wt % 90 ppm Na, 39.2 nm $SiO_2$ | 0.97 | 138 | 98.2 | 83.2 | 84.8 | 89.7 |
| 7 | $Ni_4Mg_3Fe_{0.9}Rb_{0.192}Cr_{0.05}Bi_{0.72}Ce_{1.76}Mo_{12.806}O_{51.539}$ + 50 wt % 568 ppm Na, 22 nm $SiO_2$ | 1.25 | 148 | 99.7 | 82.2 | 82.4 | 89.7 |

Notes:
1. "X/Y Ratio" is the XRD intensity ratio X/Y as described herein.
2. "HOS" is "hours on stream.
3. "% $C_3^=$ Conv" is mole percent per pass conversion of propylene to all products.
4. "% AN Yield" is percent acrylonitrile yield.
5. "% AN Sel" is percent acrylonitrile selectivity.
6. "% —CN Yield is combined percent yield of acrylonitrile, acetonitrile and hydrogen cyanide.
7. The catalysts of this are described on an "$Mo_{12}$" basis (i.e. the subscript of Mo = 12), to convert any of above compositions to the "$Mo_{12}$" basis, simply divide each subscript in the composition by the shown Mo subscript and then multiply by 12. For example, the Example 3 composition of $Ni_4Mg_3Fe_{0.9}Rb_{0.192}Cr_{0.05}Bi_{0.72}Ce_{1.76}Mo_{12.806}O_{51.539}$ is equivalent to $Ni_{3.748}Mg_{2.811}Fe_{0.843}Rb_{0.180}Cr_{0.047}Bi_{0.675}Ce_{1.65}Mo_{12}O_{48.295}$ on an "$Mo_{12}$" basis.

TABLE 3

| Ex. No. | Catalyst | Ce/Fe Ratio | Attrition Test Losses |
|---|---|---|---|
| C4 | $Ni_{7.5}Mg_3Fe_{1.8}Rb_{0.12}Cr_{0.1}Bi_{0.45}Ce_{1.1}Mo_{15.85}O_{63.835}$ + 50 wt % 27 ppm Na, 39 nm $SiO_2$ | 0.61 | Not measured |
| C5 | $Ni_{7.5}Mg_3Fe_{1.8}Rb_{0.12}Cr_{0.1}Bi_{0.45}Ce_{1.1}Mo_{15.85}O_{63.835}$ + 50 wt % 27 ppm Na, 39 nm $SiO_2$ | 0.61 | Not measured |
| C6 | $Ni_5Mg_2Fe_{1.8}Rb_{0.12}Cr_{0.1}Bi_{0.45}Ce_{1.1}Mo_{12.35}O_{49.835}$ + 50 wt % 27 ppm Na, 39 nm $SiO_2$ | 0.61 | 13.1 |
| C7 | $Ni_4Mg_3Fe_{1.8}Rb_{0.192}Cr_{0.1}Bi_{0.45}Ce_{1.1}Mo_{12.386}O_{49.979}$ + 50 wt % 90 ppm Na, 39.2 nm $SiO_2$ | 0.61 | 10.3 |
| 3 | $Ni_4Mg_3Fe_{0.9}Rb_{0.192}Cr_{0.05}Bi_{0.72}Ce_{1.76}Mo_{12.806}O_{51.539}$ + 50 wt % 27 ppm Na, 39 nm $SiO_2$ | 1.95 | 6.2 |
| 4 | $Ni_4Mg_3Fe_{0.9}Rb_{0.192}Cr_{0.05}Bi_{0.72}Ce_{1.76}Mo_{12.335}O_{50.126}$ + 50 wt % 27 ppm Na, 39 nm $SiO_2$ | 1.95 | 7.2 |
| 5 | $Ni_{4.26}Mg_{3.195}Fe_{0.9}Rb_{0.192}Cr_{0.05}Bi_{0.72}Ce_{1.76}Mo_{12.806}O_{51.994}$ + 50 wt % 27 ppm Na, 39 nm $SiO_2$ | 1.95 | 6.1 |
| 6 | $Ni_4Mg_3Fe_{0.9}Rb_{0.192}Cr_{0.05}Bi_{0.72}Ce_{1.76}Mo_{12.50}O_{50.627}$ + 50 wt % 90 ppm Na, 39.2 nm $SiO_2$ | 1.95 | 7.1 |

TABLE 3-continued

| Ex. No. | Catalyst | Ce/Fe Ratio | Attrition Test Losses |
|---|---|---|---|
| 7 | $Ni_4Mg_3Fe_{0.9}Rb_{0.192}Cr_{0.05}Bi_{0.72}Ce_{1.76}Mo_{12.806}O_{51.539}$ + 50 wt % 568 ppm Na, 22 nm $SiO_2$ | 1.95 | 4.9 |

Notes:
1. "Attrition Test Losses" is the result of a submerged jet attrition test and the numerical value is the percent loss of catalyst for the period between 0 and 20 hrs. This is a measure of overall catalyst particle strength. Lower attrition numbers are desirable. Attrition numbers above about 8.0 are not preferred for commercial catalysts due to greater catalyst loss rate. The submerged jet is as described in the ASTM standard attrition test.

As can be seen from Tables 2 and 3, the catalyst compositions as defined by the instant invention (note the X/Y ratio) exhibit (i) higher overall to acrylonitrile, acetonitrile and RCN when propylene was ammoxidized over such catalyst at elevated temperatures in the presence of ammonia and air and (ii) lower attritions losses (greater particle strength), compared to similar catalysts outside the scope of the instant invention.

COMPARATIVE EXAMPLES C8 and EXAMPLES 8-11

Various catalyst formulations were prepared by techniques as described herein. For such formulations, Table 4, illustrates the catalysts with Ce/Fe ratios less than about 0.7 have poorer attrition as opposed to catalysts with higher Ce/Fe ratios.

TABLE 4

| Ex. No. | Catalyst | Ce/Fe Ratio | Attrition Results 0-20 hr |
|---|---|---|---|
| C8 | $Ni_5Mg_2Fe_{1.8}Rb_{0.12}Cr_{0.1}Bi_{0.45}Ce_{1.1}Mo_{12.35}O_{49.835}$ + 50 wt % 27 ppm Na, 39 nm $SiO_2$ | 0.611 | 12.82 |
| 8 | $Ni_5Mg_2Fe_{0.9}Rb_{0.12}Cr_{0.05}Bi_{0.45}Ce_{1.1}Mo_{11.375}O_{45.485}$ + 50 wt % 27 ppm Na, 39 nm $SiO_2$ | 1.222 | 6.98 |
| 9 | $Ni_4Mg_3Fe_{0.9}Rb_{0.192}Cr_{0.05}Bi_{0.72}Ce_{1.76}Mo_{12.806}O_{51.539}$ + 50 wt % 27 ppm Na, 39 nm $SiO_2$ | 1.956 | 6.32 |
| 10 | $Ni_4Mg_3Fe_{0.9}Rb_{0.18}Cr_{0.05}Bi_{0.58}Ce_{1.75}Mo_{12.575}O_{50.61}$ + 50 wt % 27 ppm Na, 39 nm $SiO_2$ | 1.944 | 6.35 |
| 11 | $Ni_4Mg_3Fe_{0.9}Rb_{0.12}Cr_{0.05}Bi_{0.72}Ce_{1.76}Mo_{12.77}O_{51.395}$ + 50 wt % 27 ppm Na, 39 nm $SiO_2$ | 1.956 | 7.60 |

While the foregoing description and the above embodiments are typical for the practice of the instant invention, it is evident that many alternatives, modifications, and variations will be apparent to those skilled in the art in light of this description. Accordingly, it is intended that all such alternatives, modifications and variations are embraced by and fall within the spirit and broad scope of the appended claims.

The claimed invention is:

1. A catalytic composition comprising a complex of metal oxides wherein the relative ratios of the elements in said catalyst are represented by the following formula:

$$Mo_{12}Bi_aFe_bA_cD_dE_eF_fG_gCe_hO_x$$

wherein A is at least one element selected from the group consisting of sodium, potassium, rubidium and cesium; and D is at least one element selected from the group consisting of nickel, cobalt, manganese, zinc, magnesium, calcium, strontium, cadmium and barium;

E is at least one element selected from the group consisting of chromium, tungsten, boron, aluminum, gallium, indium, phosphorus, arsenic, antimony, vanadium and tellurium;

F is at least one element selected from the group consisting of a rare earth element, titanium, zirconium, hafnium, niobium, tantalum, aluminum, gallium, indium, thallium, silicon, germanium, and lead;

G is at least one element selected from the group consisting of silver, gold, ruthenium, rhodium, palladium, osmium, iridium, platinum and mercury; and a, b, c, d, e, f, g, h and n are, respectively, the atomic ratios of bismuth (Bi), iron (Fe), A, D, E, F, cerium (Ce) and oxygen (O), relative to 12 atoms of molybdenum (Mo), wherein a is from 0.05 to 7, b is from 0.1 to 7, c is from 0.01 to 5, d is from 0.1 to 12, e is from 0 to 5, f is from 0 to 5, g is from 0 to 0.2, h is from 0.01 to 5, and x is the number of oxygen atoms required to satisfy the valence requirements of the other component elements present;

wherein $0.8 \leq h/b \leq 5$, and wherein the catalyst composition comprises a support selected from the group consisting of silica, alumina, zirconium, titania, or mixtures thereof, and wherein the support comprises between 30 and 70 weight percent of the catalyst composition.

2. The catalytic composition of claim 1, wherein $1 \leq h/b \leq 3$.

3. The catalytic composition of claim 1, wherein $1.5 \leq h/b \leq 2$.

4. A process for the conversion of an olefin selected from the group consisting of propylene, isobutylene or mixtures thereof, to acrylonitrile, methacrylonitrile, and mixtures thereof, respectively, by reacting in the vapor phase at an elevated temperature and pressure said olefin with a molecular oxygen containing gas and ammonia in the presence of a catalyst wherein the relative ratios of the elements in said catalyst are represented by the following formula:

$$Mo_{12}Bi_aFe_bA_cD_dE_eF_fG_gCe_hO_x$$

wherein A is at least one element selected from the group consisting of sodium, potassium, rubidium and cesium; and D is at least one element selected from the group consisting of nickel, cobalt, manganese, zinc, magnesium, calcium, strontium, cadmium and barium;

E is at least one element selected from the group consisting of chromium, tungsten, boron, aluminum, gallium, indium, phosphorus, arsenic, antimony, vanadium and tellurium;

F is at least one element selected from the group consisting of a rare earth element, titanium, zirconium, hafnium, niobium, tantalum, aluminum, gallium, indium, thallium, silicon, germanium, and lead;

G is at least one element selected from the group consisting of silver, gold, ruthenium, rhodium, palladium, osmium, iridium, platinum and mercury; and a, b, c, d, e, f, g, h and n are, respectively, the atomic ratios of bismuth (Bi), iron (Fe), A, D, E, F, cerium (Ce) and oxygen (O), relative to 12 atoms of molybdenum (Mo), wherein a is from 0.05 to 7,
b is from 0.1 to 7,
c is from 0.01 to 5,
d is from 0.1 to 12,
e is from 0 to 5,
f is from 0 to 5,
g is from 0 to 0.2,
h is from 0.01 to 5, and
x is the number of oxygen atoms required to satisfy the valence requirements of the other component elements present;

wherein $0.8 \leq h/b \leq 5$, and wherein the catalyst composition comprises a support selected from the group consisting of silica, alumina, zirconium, titania, or mixtures thereof, and wherein the support comprises between 30 and 70 weight percent of the catalyst composition.

5. The process of claim 4, wherein $1 \leq h/b \leq 3$.

6. The process of claim 5, wherein $1.5 \leq h/b \leq 2$.

* * * * *